US007201163B2

(12) United States Patent
Jiang et al.

(10) Patent No.: US 7,201,163 B2
(45) Date of Patent: Apr. 10, 2007

(54) METHOD FOR ALTERING THE BODY TEMPERATURE OF A PATIENT USING A NEBULIZED MIST

(75) Inventors: Yandong Jiang, Newton, MA (US); Massimo Ferrigno, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 582 days.

(21) Appl. No.: 10/337,417

(22) Filed: Jan. 7, 2003

(65) Prior Publication Data

US 2003/0136402 A1 Jul. 24, 2003

Related U.S. Application Data

(60) Provisional application No. 60/346,289, filed on Jan. 9, 2002.

(51) Int. Cl.
*A61M 11/00* (2006.01)

(52) U.S. Cl. ............................ 128/200.21; 128/200.14

(58) Field of Classification Search ........... 128/200.14, 128/200.18, 200.21, 200.23, 913, 898, 203.12, 128/203.15, 203.16, 203.17, 203.26, 204.14, 128/204.15, 204.17; 514/958, 959; 604/23, 604/24, 514; 607/105; 252/372
See application file for complete search history.

(56) References Cited

U.S. PATENT DOCUMENTS

| | | | | |
|---|---|---|---|---|
| 3,812,854 | A * | 5/1974 | Michaels et al. | 128/200.16 |
| 4,595,002 | A * | 6/1986 | Michaels et al. | 128/200.21 |
| 5,335,650 | A | 8/1994 | Shaffer et al. | 128/200.24 |
| 5,456,702 | A * | 10/1995 | Falk | 607/105 |
| 5,490,498 | A * | 2/1996 | Faithfull et al. | 128/203.12 |
| 5,492,109 | A * | 2/1996 | Hirschl et al. | 128/201.21 |
| 5,540,225 | A | 7/1996 | Schutt | 128/207.15 |
| 5,938,118 | A | 8/1999 | Cooper | 239/102.2 |
| 6,041,777 | A * | 3/2000 | Faithfull et al. | 128/200.24 |
| 6,303,156 | B1 | 10/2001 | Ferrigno | 424/673 |
| 6,514,245 | B1 * | 2/2003 | Williams et al. | 606/21 |
| 6,576,191 | B1 * | 6/2003 | Myrick et al. | 422/45 |
| 6,613,280 | B2 * | 9/2003 | Myrick et al. | 422/45 |
| 6,694,977 | B1 * | 2/2004 | Federowicz et al. | 128/204.18 |
| 2003/0131844 | A1 * | 7/2003 | Kumar et al. | 128/200.24 |

FOREIGN PATENT DOCUMENTS

WO WO 99/66938 * 12/1999

OTHER PUBLICATIONS

Beran, et al., "Hypothermia and Rewarming Induced by Surface and He-$O_2$, Inhalate Temperature Control," *J. Applied Physiol. 39*:337-340 (1975).
Forman, et al., "A New Approach to Induced Hypothermia," *J. Surgical Res. 40*:36-42 (1986).
Ingenito, et al., "Dissociation of Temperature-Gradient and Evaporative Heat Loss, During Cold Gas Hyperventilation in Cold-Induced Asthma," *Am. Rev. Respir. Dis. 138*:540-546 (1988).

* cited by examiner

*Primary Examiner*—Justine Yu
(74) *Attorney, Agent, or Firm*—Michael A. Sanzo; Law Office of Michael A. Sanzo, LLC

(57) ABSTRACT

Methods for changing the body temperature of a patient by having them breathe a mist created by nebulizer. The temperature of the mist is adjusted using a heat exchanger. The methods may be used to either cool or warm patients for a variety of clinical reasons. In addition, the invention includes a device (Thermomist) that can be used for generating a mist that can be administered to patients.

13 Claims, 2 Drawing Sheets

METHOD FOR ALTERING THE BODY TEMPERATURE OF A PATIENT USING A NEBULIZED MIST

CROSS REFERENCE TO RELATED APPLICATION

The present application claims the benefit of U.S. provisional application No. 60/346,289, filed Jan. 9, 2002.

FIELD OF THE INVENTION

The present invention is directed to a noninvasive method for rapidly changing the body temperature of a patient. This is accomplished by having the patient breathe a mist having a temperature either above or below the patient's body temperature. In addition, the invention includes a specialized nebulizer that can be used to produce a mist in which liquid particles are of very small diameter.

BACKGROUND OF THE INVENTION

Hypothermia is routinely induced by physicians to protect the heart and brain of patients during cardiac surgery or operations involving cerebral blood vessels. Physicians may also rapidly cool a patient's body to protect brain tissue following traumatic injury, during resuscitation from cardiac arrest, and to help prevent brain damage after a stroke. In other instances, the rapid warming of a patient can be important, e.g., in cases where hypothermia has resulted from an accident.

At present, cardio-pulmonary bypass (CPB) is the most effective method for rapidly changing a patient's core temperature. However, CPB is invasive and requires sophisticated equipment and well trained personnel. Non-invasive approaches to changing core temperature currently in use rely upon surface cooling or heating by covering a patient's body with a blanket in which either air or water is circulated.

Another approach has been to use the respiratory system for heat exchange. Because liquids generally have higher specific heats than gases, ventilation of patients with a liquid provides one attractive alternative for controlling body temperature (see Forman, et al., *J Surg. Res.* 40:36–42 (1986)). However, minute ventilation with a liquid is limited by its high viscosity and this, in turn, leads to severe $CO_2$ retention by patients. Moreover, liquids tend to wash out surfactants from the alveoli of lungs, thereby causing injury.

These problems are avoided when a gas is used for inhalation. However, the specific heat of gases tends to be low and, consequently, heat exchange is relatively slow. A significant advance in methods of controlling body temperature would result from the development of procedures in which patients inhale mixtures having both a high specific heat and low viscosity.

SUMMARY OF THE INVENTION

The present invention is based upon the concept that a patient's body temperature can be rapidly changed by having them inhale nebulized mists that are at a temperature either above or below that of the patient. The mists are distinguished from gases containing water vapor by the presence of distinct liquid particles of small diameter, typically 1–5 microns. The mists have a low viscosity due to their gas component and a high specific heat due to their liquid component.

In a first aspect, the invention is directed to a method for reducing the body temperature of a patient for any clinical condition in which such a reduction is desirable. The method involves administering a precooled mist to the patient who breathes it. The mist is generated by a nebulizer and contains liquid particles that, on average, are no more than 5 microns in diameter, and preferably no more than 2 microns in diameter. The mist is comprised of a physiologically acceptable gas and a physiologically acceptable liquid and is administered at a temperature below the temperature of the patient. Administration is maintained until body temperature is reduced to a desired temperature.

Typically, cooling mists will be made up of no less than 80% gas by volume and no more than 20% liquid. Preferred gases include air, oxygen or a combination of the two gases. Preferred liquids are water and saline. This procedure may be used to cool a patient's body for, or during, cardiac surgery or neurosurgery. In addition, the body temperature of a patient may be cooled as a treatment for hemorrhagic shock or to prevent brain damage subsequent to a stroke.

The method discussed above can, alternatively, be used for increasing the body temperature of a patient. The only significant difference is that the mist delivered to a patient should be at a temperature higher than that patient's body temperature. As with the procedure discussed above, particle size should be no greater than 5 microns and preferably no greater than 2 microns. The same gases and liquids described above may also be used for increasing the body temperature of a patient. This procedure may be used as a treatment for hypothermia.

In another aspect, the invention is directed to a heat exchange system ("Thermomist") including an ultrasonic nebulizer which is specifically designed to produce a mist having particles of small size (see FIGS. 1 and 2). The nebulizer contains a gas-impermeable tubing in which the mist is circulated (31). Any type of tubing may be used for this purpose, however metal tubing such as copper is generally preferred. The Thermomist has an interface (either a mask or connector for an endotracheal tube) which may be used for spontaneous or mechanical ventilation of a patient with the mist from the nebulizer and which is connected to a mist generation region (28) by means of an exhaled gas inlet tube (26). The exhaled gas inlet tube has a gas supply inlet (11) that is connected to a gas reservoir (27). The Thermomist also has a mist generation region (28) that connects the exhaled gas inlet tube (26) to a heat exchange region (29). The mist generation region (28) is bounded on the bottom by a fluid layer (3) lying on the surface of a mist generation plate (1A). Mist is carried from the mist generation region (28) to a heat exchange region (29) in which the tubing containing mist extends through a heat exchanger (22) and connects to the inhalation limb (25). The inhalation limb of the breathing circuit (25) connects the heat exchange region to the interface (30) through a ventilator (21) during mechanical ventilation, or a breathing bag (not shown in FIGS. 1 and 2) during spontaneous ventilation. The system has a fluid trap (24) connected to an overflow liquid reservoir (6) and it also includes temperature sensors (19, 20) in the inspiratory (25) and expiratory (26) limbs of the breathing cicuit.

The nebulizer in the system has a mist generation plate (1A) which lies underneath the mist generation region (28). The mist generation plate serves as an electrode and has a fluid layer (3) on its upper surface. There is a vibrator plate (2) which is in contact with the bottom surface of the mist generation plate (1A) and the top surface of an electrode (1B). An overflow tube (32) connects the fluid layer to an overflow liquid reservoir (6). Liquid in the overflow liquid reservoir (6) is pumped into the main liquid reservoir (5) by a pump (13). Then the liquid (8) in the main liquid reservoir (5) drains through a tubing (4) into the fluid layer (3). Finally, the nebulizer includes a heat exchanger (22) which surrounds the heat exchange region (29) of the system. In preferred embodiments, the ultrasonic nebulizer has a vibrator plate that vibrates at a frequency of about 5 Mhz.

BRIEF DESCRIPTION OF THE DRAWINGS

FIG. 1 shows a heat exchange system (Thermomist) that can be used for creating and delivering mist to a patient.

FIG. 2 is an isolated view of the circulation of the mist in the system described in FIG. 1.

Figure 1:
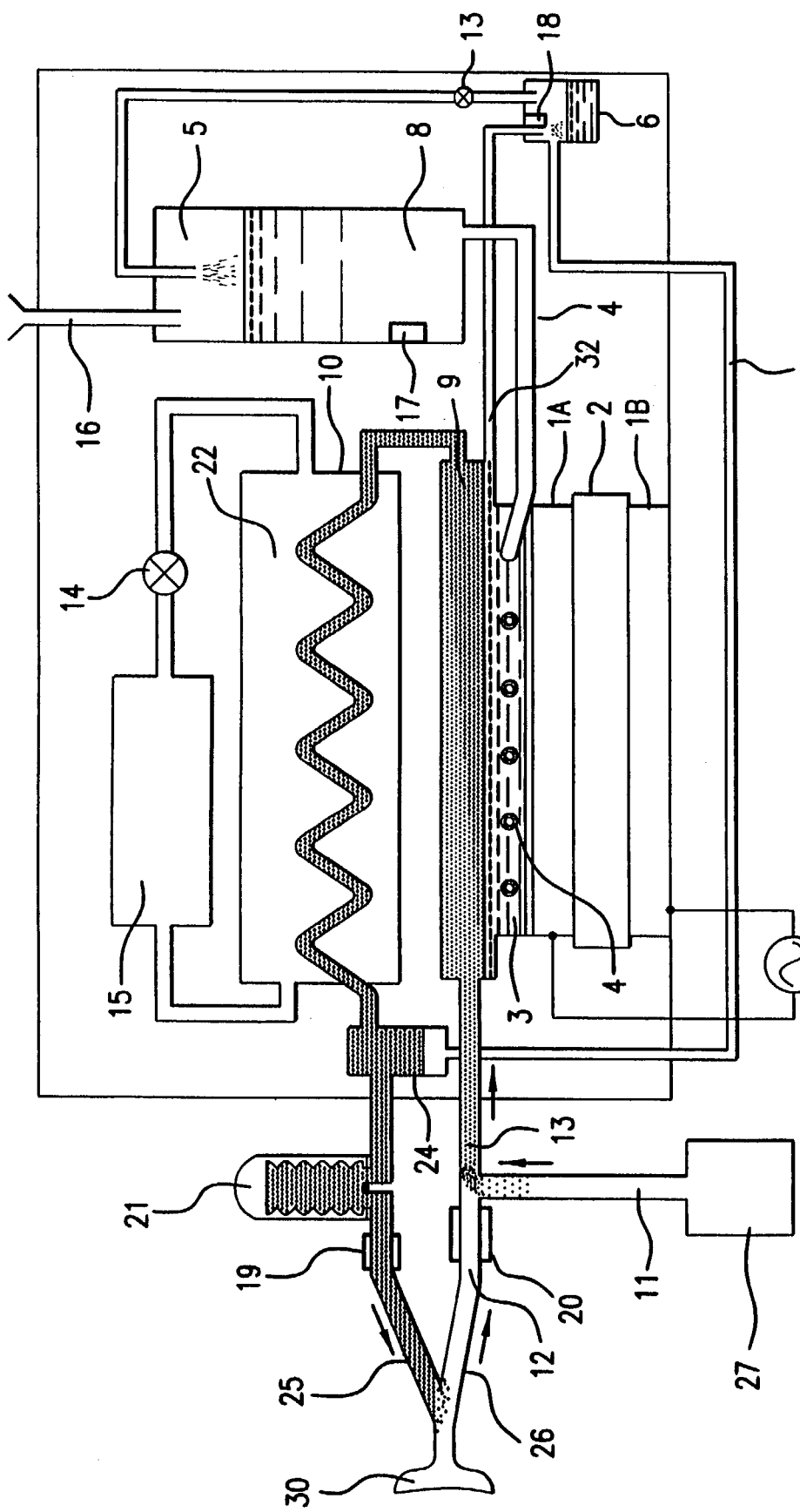
FIG. 1.

The main components shown in the drawings are as follows:

| | |
|---|---|
| 1A: | Mist generation plate/electrode |
| 1B: | Electrode |
| 2: | Vibrator plate |
| 3: | Fluid layer |
| 4: | Liquid reservoir tubing |
| 5: | Main liquid reservoir |
| 6: | Overflow liquid reservoir |
| 7: | Mist condensate collected by gravity |
| 8: | Liquid in main reservoir |
| 9: | Mist |
| 10: | Heat exchange liquid |
| 11: | Fresh gas supply inlet |
| 12: | Gas exhaled by patient |
| 13: | Pump |
| 14: | Pump to circulate heat exchange liquid |
| 15: | Control unit for heat exchanger |
| 16: | Fill tube for main liquid reservoir |
| 17: | Liquid level sensor |
| 18: | Liquid flow sensor |
| 19: | Temperature sensor A |
| 20: | Temperature sensor B |
| 21: | Ventilator |
| 22: | Heat exchanger |
| 23: | High frequency generator |
| 24: | Liquid trap |
| 25: | Inhalation limb of breathing circuit |
| 26: | Exhalation limb of breathing circuit |
| 27: | Fresh gas reservoir |
| 28: | Mist generation region of the system |
| 29: | Heat exchange region of the system |
| 30: | Interface between patient and the system |
| 31: | Tubing connecting 28 and 29 |
| 32: | Overflow tube |

DETAILED DESCRIPTION OF THE INVENTION

The present invention provides a simple method for rapidly changing the body temperature of a patient. This is accomplished by having the patient breathe, either spontaneously or with the help of a ventilator, a mist that has been either cooled or warmed to a desired temperature. The mist is prepared using a nebulizer and may be distinguished from gases containing, for example, water vapor by the presence of liquid droplets of a controlled size. The droplets must be less than 5 microns in diameter and, preferably, are less than 2 microns in diameter.

The convective component of respiratory heat exchange is directly proportional to the minute ventilation, the density and specific heat of the breathing mixture and the difference in temperature between the exhaled and inhaled mixture. Thus, respiratory heat exchange is maximized by:

1. Increasing minute ventilation: This can be achieved by asking a patient to increase his/her tidal volume and respiratory rate and/or by using a standard operating room or ICU ventilator in an intubated patient. The patient may be asked to hyperventilate spontaneously prior to being sedated and intubated to achieve faster rates of cooling or warming. If eucapnia (also known as isocapnia) is desired, carbon dioxide can be added to the breathing mixture as guided by carbon dioxide pressure in either end-tidal gas or arterial blood of the patient.
2. Increasing the density of the breathing mixture: for example, a high concentration of sulfur hexafluoride in a gas mixture would result in higher gas density and a more rapid rate of heat exchange.
3. Increasing the specific heat of the breathing mixture: in the present invention, this is accomplished by adding a liquid to inhaled compositions
4. Increasing the difference in temperature between exhaled and inhaled gas: In order to cool a patient, the breathing mixture to be inhaled must be cooled below the patient's body temperature. The colder the inhaled breathing mixture, the higher the resulting respiratory heat loss. In order to warm a patient, the breathing mixture to be inhaled must be warmed above body temperature. The warmer the inhaled breathing mixture, the higher the resulting respiratory heat gain.

Any commercially available nebulizer is compatible for use in the present invention provided it can create a mist with an average particle diameter of less than 5 microns. If the nebulizer does not include means for controlling the temperature of mist, then a separate device will have to be used for this purpose. For example, the mist created by the nebulizer could be passed though a separate heat exchanger prior to delivery to a patient.

The degree to which a patient is cooled or warmed will be determined by clinical considerations on a case by case basis. Reducing body temperature will be desirable for patients undergoing cardiac surgery or neurosurgery, as a treatment for stroke or to reduce the amount of damage that occurs subsequent to a stroke. Mists may be administered at a temperature only slightly below body temperature, e.g., at 30° C., or, alternatively, may be administered at near-freezing temperatures. Warmed preparations (e.g., at a temperature up to 42° C.) of mist will be desirable for hypothermic patients.

Any physiologically acceptable gas and liquid may be used for the creation of mist. Preferred gases are air and oxygen, or a combination of the two gases. Preferred liquids for the generation of mist include water and saline. In general, the mist should comprise no less than 80% (typically 80–95%) gas by volume and no more than 20% (typically 5-20%) liquid.

Figure 2:
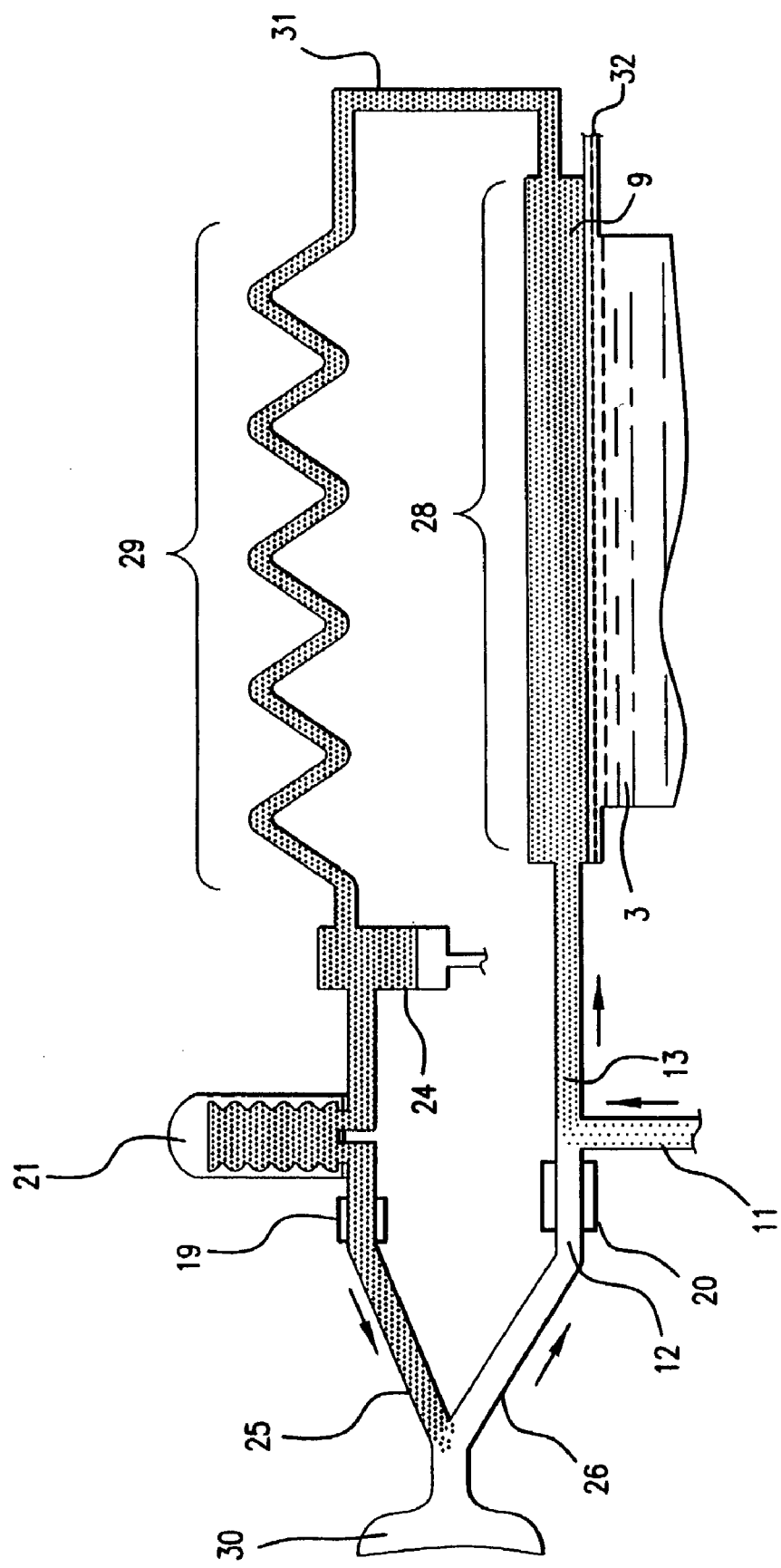
FIG. 2.

In addition to methods for altering a patient's body temperature, the invention includes a device ("Thermomist") that can be used for creating and delivering mists to a patient. The main components making up the device are shown in FIGS. 1 and 2. The device includes an interface (30) that allows a patient to breathe the temperature-adjusted mist created by the device. The patient's exhaled gas (12) passes into an exhalation limb of the breathing circuit (26). The exhaled gas passes through a temperature sensor (20) and is mixed with fresh gas through an inlet port (11)

connected to a gas reservoir (27). The mixture of expired gas and fresh gas next passes into a mist generation region (28) of the Thermomist.

In this region, mist is created using a generator that produces a frequency of about 5 Mhz through its electrodes (1A and 1B). Vibration is generated through a piezoelectric vibrator (2) at the same frequency as that of the electrodes. The surface of one of the electrodes (1A, designated as a "mist generation plate") is covered by a thin layer of fluid (3) at a depth of about 1 or 2 centimeters. Mist is created by the mist generation plate vibrating in the direction of its thickness. As fluid is converted into mist, it is replaced on the surface of the plate (1A) from the main liquid reservoir (5) connected to the fluid layer (3) by tubing (4). The portion of the tubing (4) over the plate (1A) has multiple small holes in its wall through which liquid flows from the lumen of the tube onto the operation surface. In this manner, the depth of the fluid layer (3) is kept constant.

Overflow liquid from the fluid layer (3) flows through an overflow tube (32) to an overflow reservoir (6). The flow of liquid may be detected with a sensor (18) before it reaches the overflow reservoir (6) and, in the case of no flow, a feedback system will be triggered to drain liquid (8) from the main reservoir (5) onto the surface of the mist generation plate (1A).

After mist has been generated, it is passed through a heat exchange region (29) of the system. In this region, the temperature of the mist is cooled or elevated as tubing carries it through a heat exchanger (22) filled with a heat exchange liquid (10). A control unit (15) regulates the temperature of the heat exchange liquid (10) which is recirculated by means of a pump (14).

After leaving the heat exchanger, the mist passes into the inspiratory limb of the breathing circuit (25) which is connected to interface (30) between the system and the patient. Prior to the inspiratory limb, there is a liquid trap (24) in which liquid, condensed in the lumen of the tubing, flows by gravity. This condensate (7) is then carried by an overflow tube to an overflow reservoir (6). The mist passes through a ventilator (21) and then into a patient's lungs during inhalation, its temperature being measured by a temperature sensor (19). The two temperature sensors (19, 20) provide parameters that may be fed into the heat exchange system (15) to modify the temperature of the heat exchange liquid (10). A one-way vale and pressure-relief system is built into the ventilator to avoid pressure build up in the system.

The right side of FIG. 1 shows tubing that leads from the overflow reservoir (6) into the fluid reservoir (5). Fluid exchange may take place through the activation of a pump (13). The fluid reservoir (5) is also equipped with a sensor (17) that is triggered if fluid levels drop below the level of the sensor. When this occurs, the sensor will remind the machine operator to add more fluid into the reservoir (5) through a fill tube (16).

One of skill in the art will recognize that the Thermomist shown in FIGS. 1 and 2 may undergo numerous rearrangements and additions without changing its basic concept. Although the system shown may be used in the temperature-altering procedures discussed above, other types of devices may be used as well. The essential components are: means for the device exchanging mist with a patient; means for creating a mist; and means for controlling the temperature of the mist.

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A method of reducing the body temperature of a patient for any clinical condition in which a reduction in body temperature is desirable, comprising:
- (a) administering a mist to said patient by ventilation, wherein:
  - (i) said mist is generated by a nebulizer and contains liquid particles having an average size of no more than 5 microns in diameter;
  - (ii) said mist comprises a mixture of a physiologically acceptable gas and a physiologically acceptable liquid;
  - (iii) said mist is administered at a temperature below the body temperature of said patient; and
- (b) maintaining the administration of said mist until said patient's body temperature is reduced.

2. The method of claim 1, wherein said mist contains liquid particles with an average size of no more than 2 microns in diameter.

3. The method of claim 1, wherein said mist comprises no less than 80% gas by volume and no more than 20% liquid by volume.

4. The method of claim 1, wherein said gas comprises air or oxygen, or a combination of the two gases.

5. The method of any one of claims 1–4, wherein said liquid is water or saline.

6. The method of claim 5, wherein the body temperature of said patient is cooled in preparation for, or during, cardiac surgery or neurosurgery.

7. The method of claim 5, wherein the body temperature of said patient is cooled as a treatment for hemorrhagic shock or to prevent brain damage subsequent to a stroke.

8. A method of increasing the body temperature of a patient for any clinical condition in which an increase in body temperature is desirable, comprising:
- (a) administering a mist to said patient by ventilation, wherein:
  - (i) said mist is generated by a nebulizer and contains liquid particles having an average size of no more than 5 microns in diameter;
  - (ii) said mist comprises a mixture of a physiologically acceptable gas and a physiologically acceptable liquid;
  - (iii) said mist is administered at a temperature above the body temperature of said patient;
- (b) maintaining the administration of said mist until said patient's body temperature is increased.

9. The method of claim 8, wherein said mist contains particles having an average size of no more than 2 microns in diameter.

10. The method of claim 8, wherein said mist comprises no less than 89% gas by volume and no more than 20% liquid by volume.

11. The method of claim 8, wherein said gas comprises air or oxygen, or a combination of the two gases.

12. The method of any one of claims 8–11, wherein said liquid is water or saline.

13. The method of claim 12, wherein the body temperature of said patient is increased as a treatment for hypothermia.

* * * * *